United States Patent
Field

(10) Patent No.: US 10,478,150 B2
(45) Date of Patent: *Nov. 19, 2019

(54) MEDICO—SURGICAL DEVICES

(71) Applicant: The Cooper Companies Global Holdings LP, St. Michael (BB)

(72) Inventor: Stephen James Field, Kent (GB)

(73) Assignee: The Cooper Companies Global Holdings LP, St. Michael (BB)

( * ) Notice: Subject to any disclaimer, the term of this patent is extended or adjusted under 35 U.S.C. 154(b) by 314 days.

This patent is subject to a terminal disclaimer.

(21) Appl. No.: 15/658,456

(22) Filed: Jul. 25, 2017

(65) Prior Publication Data

US 2018/0064414 A1 Mar. 8, 2018

Related U.S. Application Data

(63) Continuation of application No. 13/064,382, filed on Mar. 22, 2011, now Pat. No. 9,743,904, which is a
(Continued)

(30) Foreign Application Priority Data

Aug. 24, 2001 (GB) .................................. 0120645.7

(51) Int. Cl.
*A61B 8/08* (2006.01)
*A61M 5/00* (2006.01)
(Continued)

(52) U.S. Cl.
CPC .............. *A61B 8/0841* (2013.01); *A61B 8/00* (2013.01); *A61B 8/14* (2013.01); *A61B 17/435* (2013.01);
(Continued)

(58) Field of Classification Search
CPC . A61B 17/435; A61B 2090/3925; A61B 8/00; A61B 8/0841; A61B 8/14;
(Continued)

(56) References Cited

U.S. PATENT DOCUMENTS 2,702,034 A 2/1955 Walter
2,740,192 A 4/1956 Ogle
(Continued)

FOREIGN PATENT DOCUMENTS

DE 38 33 365 4/1989
DE 39 36 162 6/1991
(Continued)

OTHER PUBLICATIONS

Demand for Invalidation Trial to the Commissioner of the Japan Patent Office re Appeal Case for Invalidating JP U.S. Pat. No. 4724372 dated Jan. 28, 2019.
(Continued)

*Primary Examiner* — Christine H Matthews
*Assistant Examiner* — Joshua Daryl D Lannu
(74) *Attorney, Agent, or Firm* — Fish & Richardson P.C.

(57) ABSTRACT

An embryo replacement catheter has a flexible extruded shaft of a transparent polyurethane with a bore extending along its length. Gas bubbles of a diameter in the range 5μ to 10μ are incorporated into the thickness of the wall of the shaft by adding gas during extrusion. The bubbles are selected to increase the visibility of the catheter under ultrasound imaging whilst still enabling material flowing along the catheter to be seen.

17 Claims, 1 Drawing Sheet

Related U.S. Application Data continuation of application No. 10/196,151, filed on Jul. 17, 2002, now Pat. No. 8,092,390.

(51) Int. Cl.

| | |
|---|---|
| *A61B 8/00* | (2006.01) |
| *A61B 8/14* | (2006.01) |
| *A61M 25/01* | (2006.01) |
| *A61M 25/00* | (2006.01) |
| *A61L 31/18* | (2006.01) |
| *A61L 29/18* | (2006.01) |
| *A61K 49/22* | (2006.01) |
| *A61B 17/435* | (2006.01) |
| *A61B 90/00* | (2016.01) |

(52) U.S. Cl.
CPC ............ *A61K 49/223* (2013.01); *A61L 29/18* (2013.01); *A61L 31/18* (2013.01); *A61M 5/00* (2013.01); *A61M 25/007* (2013.01); *A61M 25/0009* (2013.01); *A61M 25/0012* (2013.01); *A61M 25/01* (2013.01); *A61B 2090/3925* (2016.02); *A61M 25/0043* (2013.01); *A61M 2210/1433* (2013.01)

(58) Field of Classification Search
CPC .... A61L 29/18; A61L 31/18; A61M 25/0009; A61M 25/0043; A61M 2210/1433; A61M 25/01; A61M 5/00; A61M 25/0012; A61M 25/007; A61K 49/223
See application file for complete search history.

(56) References Cited

U.S. PATENT DOCUMENTS

| | | |
|---|---|---|
| 2,989,053 A | 6/1961 | Hamilton |
| 3,093,134 A | 6/1963 | Roehr |
| 3,605,750 A | 9/1971 | Sheridan et al. |
| 3,720,210 A | 3/1973 | Diettrich |
| 4,265,251 A | 5/1981 | Tickner |
| 4,386,628 A | 6/1983 | Stanley |
| 4,582,061 A | 4/1986 | Fry |
| 4,644,977 A | 2/1987 | Arterburn |
| 4,701,161 A | 10/1987 | Lenck |
| 4,731,052 A | 3/1988 | Seitz, Jr. |
| 4,805,628 A | 2/1989 | Fry et al. |
| 4,809,860 A | 3/1989 | Allen |
| 4,810,244 A | 3/1989 | Allen |
| 4,824,434 A | 4/1989 | Seitz, Jr. |
| 4,832,681 A | 5/1989 | Lenck |
| 4,869,259 A | 9/1989 | Elkins |
| 4,874,649 A | 10/1989 | Daubenbüchel et al. |
| 4,877,033 A | 10/1989 | Seitz, Jr. |
| 4,887,615 A | 12/1989 | Taylor |
| 5,048,530 A | 9/1991 | Hurwitz |
| 5,071,425 A | 12/1991 | Gifford, III et al. |
| 5,081,997 A | 1/1992 | Bosley, Jr. et al. |
| 5,090,414 A | 2/1992 | Takano |
| 5,149,328 A | 9/1992 | Zaha |
| 5,160,319 A | 11/1992 | Emery et al. |
| 5,195,979 A | 3/1993 | Schinkel et al. |
| 5,201,314 A * | 4/1993 | Bosley, Jr. ............. A01K 85/00 600/431 |
| 5,211,627 A | 5/1993 | William |
| 5,250,649 A | 10/1993 | Onwumere et al. |
| 5,259,837 A | 11/1993 | Van Wormer |
| 5,273,527 A | 12/1993 | Schatz et al. |
| 5,289,831 A | 3/1994 | Bosley |
| 5,312,376 A * | 5/1994 | Van Heugten .... A61M 25/0693 604/168.01 |
| 5,327,891 A | 7/1994 | Rammler |
| 5,342,309 A | 8/1994 | Hausser |
| 5,360,389 A | 11/1994 | Chenette |
| 5,383,466 A | 1/1995 | Partika |
| 5,405,321 A | 4/1995 | Reeves |
| 5,415,634 A | 5/1995 | Glynn et al. |
| 5,596,990 A | 1/1997 | Yock et al. |
| 5,611,345 A | 3/1997 | Hibbeln |
| 5,622,665 A | 4/1997 | Wang |
| 5,646,194 A | 7/1997 | Kobayashi et al. |
| 5,688,490 A | 11/1997 | Tournier et al. |
| 5,724,977 A | 3/1998 | Yock et al. |
| 5,741,522 A | 4/1998 | Violante et al. |
| 5,744,092 A | 4/1998 | Halgren et al. |
| 5,759,154 A | 6/1998 | Hoyns |
| 5,766,135 A | 6/1998 | Terwilliger |
| 5,769,795 A | 6/1998 | Terwilliger |
| 5,772,642 A | 6/1998 | Ciamacco, Jr. et al. |
| 5,820,554 A | 10/1998 | Davis et al. |
| 5,820,850 A | 10/1998 | Hashimoto et al. |
| 5,827,174 A | 10/1998 | Reuss, Jr. et al. |
| 5,843,023 A | 12/1998 | Cecchi |
| 5,851,464 A | 12/1998 | Davila et al. |
| 5,851,477 A | 12/1998 | Halgren et al. |
| 5,879,305 A | 3/1999 | Yock et al. |
| 5,921,933 A | 7/1999 | Sarkis et al. |
| 5,932,154 A | 8/1999 | Csongor et al. |
| 5,932,299 A | 8/1999 | Katoot |
| 5,939,015 A | 8/1999 | Csongor |
| 5,945,061 A | 8/1999 | Csongor et al. |
| 5,967,988 A | 10/1999 | Briscoe et al. |
| 5,976,501 A | 11/1999 | Jablonski |
| 6,010,448 A | 1/2000 | Thompson |
| 6,018,676 A | 1/2000 | Davis et al. |
| 6,024,727 A | 2/2000 | Thorne et al. |
| 6,027,443 A | 2/2000 | Nag |
| 6,030,369 A | 2/2000 | Engelson et al. |
| 6,063,221 A | 5/2000 | Weinberg et al. |
| 6,071,580 A | 6/2000 | Bland et al. |
| 6,074,578 A | 6/2000 | Csongor et al. |
| 6,086,540 A | 7/2000 | Bonneville et al. |
| 6,106,473 A | 8/2000 | Violante et al. |
| 6,110,444 A | 8/2000 | Klaveness et al. |
| 6,165,165 A | 12/2000 | Cecchi et al. |
| 6,207,752 B1 | 3/2001 | Abraham et al. |
| 6,210,330 B1 | 4/2001 | Tepper |
| 6,240,960 B1 | 6/2001 | Fillmore |
| 6,261,241 B1 | 7/2001 | Burbank et al. |
| 6,277,084 B1 | 8/2001 | Abele et al. |
| 6,283,951 B1 | 9/2001 | Flaherty et al. |
| 6,290,672 B1 | 9/2001 | Abae |
| 6,306,094 B1 | 10/2001 | Joseph |
| 6,312,429 B1 | 11/2001 | Burbank et al. |
| 6,331,166 B1 | 12/2001 | Burbank et al. |
| 6,344,026 B1 | 2/2002 | Burbank et al. |
| 6,346,086 B1 | 2/2002 | Maksem et al. |
| 6,347,241 B2 | 2/2002 | Burbank et al. |
| 6,356,782 B1 | 3/2002 | Sirimanne et al. |
| 6,358,211 B1 | 3/2002 | Mamayek |
| 6,364,855 B1 | 4/2002 | Zappala |
| 6,371,904 B1 | 4/2002 | Sirimanne et al. |
| 6,371,973 B1 | 4/2002 | Tepper |
| 6,427,081 B1 | 7/2002 | Burbank et al. |
| 6,432,352 B1 | 8/2002 | Csongor |
| 6,435,189 B1 | 8/2002 | Lewis et al. |
| 6,454,727 B1 | 9/2002 | Burbank et al. |
| 6,461,302 B1 | 10/2002 | Thompson |
| 6,471,700 B1 | 10/2002 | Burbank et al. |
| 6,481,462 B2 | 11/2002 | Fillmore et al. |
| 6,497,706 B1 | 12/2002 | Burbank et al. |
| 6,506,156 B1 | 1/2003 | Jones et al. |
| 6,508,773 B2 | 1/2003 | Burbank et al. |
| 6,517,498 B1 | 2/2003 | Burbank et al. |
| 6,527,752 B1 | 3/2003 | Bosley, Jr. et al. |
| 6,540,693 B2 | 4/2003 | Burbank et al. |
| 6,540,695 B1 | 4/2003 | Burbank et al. |
| 6,544,185 B2 | 4/2003 | Montegrande |
| 6,544,230 B1 | 4/2003 | Flaherty et al. |
| 6,567,689 B2 | 5/2003 | Burbank et al. |
| 6,577,904 B1 | 6/2003 | Zhang et al. |
| 6,610,005 B1 | 8/2003 | Tao |
| 6,610,016 B1 | 8/2003 | Violante et al. |
| 6,638,234 B2 | 10/2003 | Burbank et al. |

(56) References Cited

U.S. PATENT DOCUMENTS

| | | |
|---|---|---|
| 6,656,407 B1 | 12/2003 | Halgren et al. |
| 6,659,105 B2 | 12/2003 | Burbank et al. |
| 6,662,041 B2 | 12/2003 | Burbank et al. |
| 6,673,440 B2 | 1/2004 | Douglas et al. |
| 6,676,658 B2 | 1/2004 | Burbank et al. |
| 6,679,824 B1 | 1/2004 | Reed et al. |
| 6,679,851 B2 | 1/2004 | Burbank et al. |
| 6,685,648 B2 | 2/2004 | Flaherty et al. |
| 6,689,071 B2 | 2/2004 | Burbank et al. |
| 6,695,767 B2 | 2/2004 | Martinez Garcia et al. |
| 6,695,787 B2 | 2/2004 | Hogendijk et al. |
| 6,699,206 B2 | 3/2004 | Burbank et al. |
| 6,712,775 B2 | 3/2004 | Burbank et al. |
| 6,716,179 B2 | 4/2004 | Burbank et al. |
| 6,723,052 B2 | 4/2004 | Mills |
| 6,725,083 B1 | 4/2004 | Burbank et al. |
| 6,736,409 B2 | 5/2004 | Hollenberg |
| 6,749,554 B1 | 6/2004 | Snow et al. |
| 6,758,848 B2 | 7/2004 | Burbank et al. |
| 6,761,680 B2 | 7/2004 | Terwilliger et al. |
| 6,786,858 B2 | 9/2004 | Terwilliger et al. |
| 6,838,278 B2 | 1/2005 | Fortino |
| 6,840,090 B2 | 1/2005 | Smith |
| 6,860,856 B2 | 3/2005 | Ward et al. |
| 6,862,470 B2 | 3/2005 | Burbank et al. |
| 6,875,168 B2 | 4/2005 | Bateman et al. |
| 6,875,182 B2 | 4/2005 | Wardle et al. |
| 6,905,458 B2 | 6/2005 | Choay et al. |
| 6,958,044 B2 | 10/2005 | Burbank et al. |
| 6,993,375 B2 | 1/2006 | Burbank et al. |
| 6,996,433 B2 | 2/2006 | Burbank et al. |
| 6,997,885 B2 | 2/2006 | Lubock et al. |
| 7,014,610 B2 | 3/2006 | Koulik |
| 7,047,063 B2 | 5/2006 | Burbank et al. |
| 7,060,020 B2 | 6/2006 | Terwilliger et al. |
| 7,188,537 B2 | 3/2007 | Junger |
| 7,189,206 B2 | 3/2007 | Quick et al. |
| 7,229,413 B2 | 6/2007 | Violante et al. |
| 7,229,418 B2 | 6/2007 | Burbank et al. |
| 7,229,439 B2 | 6/2007 | Burbank et al. |
| 7,235,052 B2 | 6/2007 | Kellar et al. |
| 7,258,669 B2 | 8/2007 | Russell |
| 7,261,712 B2 | 8/2007 | Burbank et al. |
| 7,264,596 B2 | 9/2007 | Burbank et al. |
| 7,282,034 B2 | 10/2007 | Burbank et al. |
| 7,322,938 B2 | 1/2008 | Burbank et al. |
| 7,322,939 B2 | 1/2008 | Burbank et al. |
| 7,322,940 B2 | 1/2008 | Burbank et al. |
| 7,329,228 B2 | 2/2008 | Burbank et al. |
| 7,357,794 B2 | 4/2008 | Makower et al. |
| 7,357,801 B2 | 4/2008 | Burbank et al. |
| 7,377,902 B2 | 5/2008 | Burbank et al. |
| 7,382,857 B2 | 6/2008 | Engel |
| 7,384,391 B2 | 6/2008 | Spittle et al. |
| 7,470,249 B2 | 12/2008 | Junger |
| 7,488,295 B2 | 2/2009 | Burbank et al. |
| 7,565,191 B2 | 7/2009 | Burbank et al. |
| 7,625,347 B2 | 12/2009 | Burbank et al. |
| 7,637,904 B2 | 12/2009 | Wingler et al. |
| 7,651,467 B2 | 1/2010 | Lubock et al. |
| 7,651,505 B2 | 1/2010 | Lubock et al. |
| 7,668,582 B2 | 2/2010 | Sirimanne et al. |
| 7,736,337 B2 | 6/2010 | Diep et al. |
| 7,792,569 B2 | 9/2010 | Burbank et al. |
| 7,794,402 B2 | 9/2010 | Wang |
| 7,819,819 B2 | 10/2010 | Quick et al. |
| 7,867,169 B2 | 1/2011 | Webler et al. |
| 7,879,011 B2 | 2/2011 | Chang |
| 7,887,737 B2 | 2/2011 | Mejlhede et al. |
| 7,970,454 B2 | 6/2011 | Jones et al. |
| 7,983,734 B2 | 7/2011 | Jones et al. |
| 8,052,669 B2 | 11/2011 | Lee-Sepsick et al. |
| 8,092,390 B2 | 1/2012 | Field |
| 8,137,346 B2 | 3/2012 | Burbank et al. |
| 8,147,487 B2 | 4/2012 | Burbank et al. |
| 8,152,737 B2 | 4/2012 | Burbank et al. |
| 8,177,792 B2 | 5/2012 | Lubock et al. |
| 8,200,313 B1 | 6/2012 | Rambod et al. |
| 8,219,182 B2 | 7/2012 | Burbank et al. |
| 8,224,424 B2 | 7/2012 | Burbank et al. |
| 8,229,553 B2 | 7/2012 | Burbank et al. |
| 8,273,009 B2 | 9/2012 | Arabia et al. |
| 8,282,573 B2 | 10/2012 | Shabaz et al. |
| 8,303,509 B2 | 11/2012 | Webler et al. |
| 8,306,602 B2 | 11/2012 | Sirimanne et al. |
| 8,320,993 B2 | 11/2012 | Sirimanne et al. |
| 8,320,994 B2 | 11/2012 | Sirimanne et al. |
| 8,343,071 B2 | 1/2013 | Shabaz et al. |
| 8,360,990 B2 | 1/2013 | Shabaz et al. |
| 8,361,082 B2 | 1/2013 | Jones et al. |
| 8,377,109 B2 | 2/2013 | Vrba et al. |
| 8,382,674 B2 | 2/2013 | Webler |
| 8,398,596 B2 | 3/2013 | Field |
| 8,430,863 B2 | 4/2013 | Webler |
| 8,460,204 B2 | 6/2013 | Quick et al. |
| 8,465,412 B2 | 6/2013 | Kamrava |
| 8,498,693 B2 | 7/2013 | Jones et al. |
| 8,560,052 B2 | 10/2013 | Mills |
| 8,585,596 B1 | 11/2013 | Flaherty et al. |
| 8,600,481 B2 | 12/2013 | Sirimanne et al. |
| 8,603,121 B2 | 12/2013 | Surti et al. |
| 8,622,887 B2 | 1/2014 | Gergeley |
| 8,626,269 B2 | 1/2014 | Jones et al. |
| 8,626,270 B2 | 1/2014 | Burbank et al. |
| 8,633,023 B2 | 1/2014 | Du et al. |
| 8,636,734 B2 | 1/2014 | Burbank et al. |
| 8,656,928 B2 | 2/2014 | Carlson et al. |
| 8,663,116 B2 | 3/2014 | Hamilton, Jr. |
| 8,672,892 B2 | 3/2014 | Carr et al. |
| 8,690,752 B2 | 4/2014 | Jose |
| 8,718,745 B2 | 5/2014 | Burbank et al. |
| 8,784,433 B2 | 7/2014 | Lubock et al. |
| 8,795,452 B2 | 8/2014 | Alpert et al. |
| 8,834,370 B2 | 9/2014 | Evert et al. |
| 8,880,154 B2 | 11/2014 | Jones et al. |
| 8,936,553 B2 | 1/2015 | Stigall et al. |
| 8,951,195 B2 | 2/2015 | Sheldon et al. |
| 8,959,753 B2 | 2/2015 | Garbini et al. |
| 8,965,486 B2 | 2/2015 | Burbank et al. |
| 9,033,889 B2 | 5/2015 | Hamilton, Jr. |
| 9,034,363 B2 | 5/2015 | Doshi et al. |
| 9,044,162 B2 | 6/2015 | Jones et al. |
| 9,044,215 B2 | 6/2015 | Shabaz et al. |
| 9,085,097 B2 | 7/2015 | Lentz et al. |
| 9,107,640 B2 | 8/2015 | Ho et al. |
| 9,149,341 B2 | 10/2015 | Jones et al. |
| 9,179,935 B2 | 11/2015 | Zarnescu et al. |
| 9,204,866 B2 | 12/2015 | Shabaz et al. |
| 9,216,012 B2 | 12/2015 | Burbank et al. |
| 9,216,037 B2 | 12/2015 | Buster et al. |
| 9,220,880 B2 | 12/2015 | Lee-Sepsick et al. |
| 9,237,937 B2 | 1/2016 | Burbank et al. |
| 9,242,076 B2 | 1/2016 | Burton et al. |
| 9,247,960 B2 | 2/2016 | Carson et al. |
| 9,320,540 B2 | 4/2016 | Badie |
| 9,636,082 B2 | 5/2017 | Field |
| 9,642,591 B2 | 5/2017 | Field et al. |
| 2002/0026117 A1 | 2/2002 | Joseph |
| 2002/0134850 A1 | 9/2002 | Hollenberg |
| 2002/0177776 A1 | 11/2002 | Crawford Keller et al. |
| 2003/0032896 A1 | 2/2003 | Bosley et al. |
| 2003/0040756 A1 | 2/2003 | Field |
| 2003/0050531 A1 | 3/2003 | Field |
| 2003/0206864 A1 | 11/2003 | Mangin |
| 2003/0208101 A1 | 11/2003 | Cecchi |
| 2004/0230119 A1 | 11/2004 | Brustad et al. |
| 2005/0074406 A1 | 4/2005 | Couvillon, Jr. et al. |
| 2005/0143656 A1 | 6/2005 | Burbank et al. |
| 2006/0089608 A1 | 4/2006 | Shaykh et al. |
| 2006/0095015 A1 | 5/2006 | Hobbs et al. |
| 2006/0106338 A1 | 5/2006 | Chang |
| 2007/0167822 A1 | 7/2007 | Webler et al. |
| 2007/0179575 A1 | 8/2007 | Esch et al. |
| 2007/0255140 A1 | 11/2007 | Violante et al. |

(56) References Cited

U.S. PATENT DOCUMENTS

| | | | |
|---|---|---|---|
| 2007/0265516 A1 | 11/2007 | Wang | |
| 2008/0058702 A1 | 3/2008 | Arndt et al. | |
| 2008/0154136 A1 | 6/2008 | Webler | |
| 2010/0256577 A1 | 10/2010 | Field | |
| 2010/0331955 A1 | 12/2010 | Vrba et al. | |
| 2013/0281835 A1 | 10/2013 | Field et al. | |

FOREIGN PATENT DOCUMENTS

| | | |
|---|---|---|
| DE | 40 14 998 | 11/1991 |
| DE | 299 08 256 | 7/1999 |
| DE | 197 27 740 | 9/1999 |
| EP | 0 033 659 | 8/1981 |
| EP | 0 072 671 | 2/1983 |
| EP | 0 083 973 | 7/1983 |
| EP | 0 109 657 | 5/1984 |
| EP | 0 131 166 | 1/1985 |
| EP | 0 243 341 | 10/1987 |
| EP | 0 323 527 | 7/1989 |
| EP | 0 356 774 | 3/1990 |
| EP | 0 382 392 | 8/1990 |
| EP | 0 386 936 | 9/1990 |
| EP | 0 481 685 | 4/1992 |
| EP | 0 526 669 | 2/1993 |
| EP | 0 552 924 | 7/1993 |
| EP | 0 567 285 | 10/1993 |
| EP | 0 586 056 | 3/1994 |
| EP | 0 624 342 | 11/1994 |
| EP | 0 701 836 | 3/1996 |
| EP | 0 935 442 | 8/1999 |
| EP | 0 941 128 | 9/1999 |
| EP | 0 995 459 | 4/2000 |
| EP | 0 996 363 | 5/2000 |
| EP | 1 105 170 | 6/2001 |
| EP | 1 109 496 | 6/2001 |
| EP | 1 118 337 | 7/2001 |
| EP | 1 132 049 | 9/2001 |
| EP | 1 139 878 | 10/2001 |
| EP | 1 146 910 | 10/2001 |
| EP | 1 152 696 | 11/2001 |
| EP | 1 155 418 | 11/2001 |
| EP | 1 166 720 | 1/2002 |
| EP | 1 173 096 | 1/2002 |
| EP | 1 177 776 | 2/2002 |
| EP | 1 189 546 | 3/2002 |
| EP | 1 196 107 | 4/2002 |
| EP | 1 274 353 | 1/2003 |
| EP | 1 358 856 | 11/2003 |
| EP | 1 450 891 | 9/2004 |
| EP | 0 941 128 | 10/2004 |
| EP | 1 491 147 | 12/2004 |
| EP | 1 494 721 | 1/2005 |
| EP | 1 513 581 | 3/2005 |
| EP | 1 525 856 | 4/2005 |
| EP | 1 599 125 | 11/2005 |
| EP | 1 626 667 | 2/2006 |
| EP | 1 667 589 | 6/2006 |
| EP | 1 696 800 | 9/2006 |
| EP | 1 781 178 | 5/2007 |
| EP | 1 919 388 | 5/2008 |
| EP | 1 967 147 | 9/2008 |
| EP | 2 103 266 | 9/2009 |
| EP | 2 114 270 | 11/2009 |
| EP | 2 174 596 | 4/2010 |
| EP | 2 319 449 | 5/2011 |
| EP | 2 389 868 | 11/2011 |
| EP | 2 407 111 | 1/2012 |
| EP | 2 407 119 | 1/2012 |
| EP | 2 517 630 | 10/2012 |
| EP | 2 555 687 | 2/2013 |
| EP | 2 564 890 | 3/2013 |
| EP | 2 570 150 | 3/2013 |
| EP | 2 620 111 | 7/2013 |
| EP | 2 641 546 | 9/2013 |
| EP | 2 984 991 | 2/2016 |
| EP | 2 995 260 | 3/2016 |
| FR | 2 716 266 | 8/1995 |
| GB | 829383 | 3/1960 |
| GB | 894653 | 4/1962 |
| GB | 1151222 | 5/1969 |
| GB | 2 263 642 | 8/1995 |
| GB | 2 274 991 | 10/1996 |
| GB | 2 381 198 | 4/2003 |
| GB | 2 388 784 | 11/2003 |
| GB | 2 380 944 | 10/2004 |
| GB | 2 379 610 | 1/2005 |
| GB | 2494395 | 1/2014 |
| GB | 2494864 | 2/2014 |
| GB | 2469839 | 9/2014 |
| JP | S 53-66986 | 6/1978 |
| JP | 55-125876 | 9/1980 |
| JP | 58-92951 | 6/1983 |
| JP | 58-198353 | 11/1983 |
| JP | 3-14451 | 2/1991 |
| JP | 06-327671 | 11/1994 |
| JP | 8-173543 | 7/1996 |
| JP | H 09-123302 | 5/1997 |
| JP | 2844238 | 1/1999 |
| JP | 2001-504101 | 3/2001 |
| JP | 2002-106759 | 4/2002 |
| JP | 2002-234066 | 8/2002 |
| JP | 2003-190275 | 7/2003 |
| SU | 1255450 | 9/1986 |
| WO | WO 94/17743 | 8/1994 |
| WO | WO 95/23615 | 9/1995 |
| WO | WO 98/19713 | 5/1998 |
| WO | WO 99/03399 | 1/1999 |
| WO | WO 00/09178 | 2/2000 |
| WO | WO 2001/13021 | 2/2001 |
| WO | WO 02/02171 | 1/2002 |

OTHER PUBLICATIONS

Coloreu, B. et al., "Embryo transfer under ultrasound guidance improves pregnancy rates after in-vitro fertilization", *Human Reproduction*, vol. 15, No. 3, pp. 616-620 (2000).

Hale, Lyndon, "Embryo transfer: how to ensure correct placement in utero", *Reproduction, Fertility and Development*, vol. 13, pp. 95-98 (2001).

Strickler, Ronald C. et al., "Ultrasound guidance for human embryo transfer", *Fertility and Sterility*, vol. 43, No. 1, pp. 54-61 (Jan. 1985).

Wood, Ellen G. et al., "Ultrasound-guided soft catheter embryo transfers will improve pregnancy rates in in-vitro fertilization", *Human Reproduction*, vol. 15, No. 1, pp. 107-112 (2000).

Woolcott, Robert et al., "Potentially important variables identified by transvaginal ultrasound-guided embryo transfer", *Human Reproduction*, vol. 12, No. 5, pp. 963-966 (1997).

\* cited by examiner

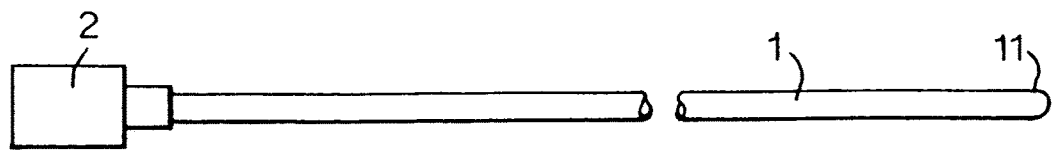
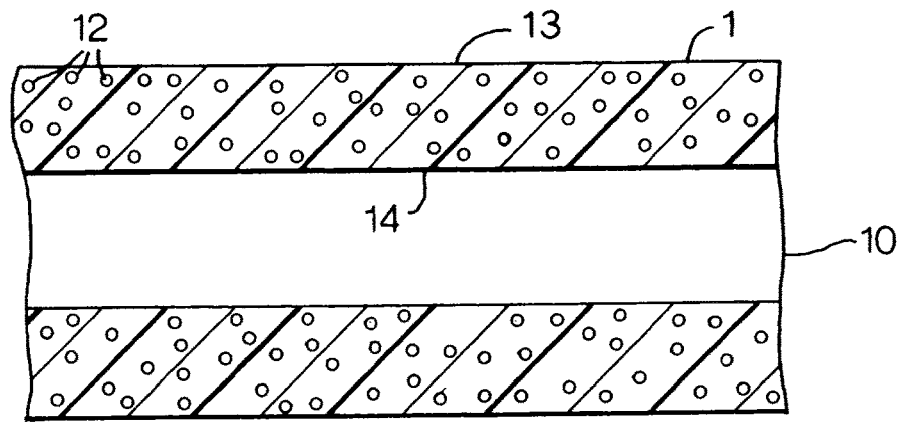
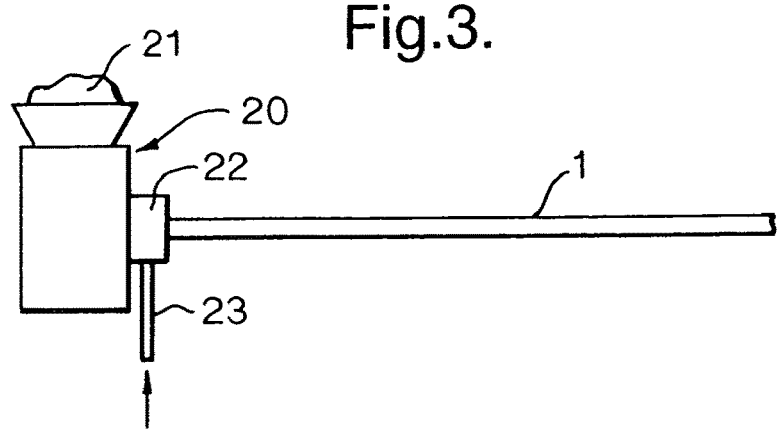
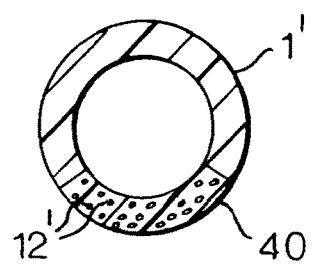

MEDICO—SURGICAL DEVICES

CROSS REFERENCE TO RELATED APPLICATIONS

This application is a continuation of, and claims priority to U.S. application Ser. No. 13/064,382, filed on Mar. 22, 2011, which is a continuation of U.S. application Ser. No. 10/196,151, filed on Jul. 17, 2002, now U.S. Pat. No. 8,092,390, which claims the benefit of United Kingdom patent application serial number 0120645.7, filed on Aug. 24, 2001. The contents of these applications are hereby incorporated by reference in its entirety.

BACKGROUND OF THE INVENTION

This invention relates to medico-surgical devices.

The invention is more particularly concerned with medico-surgical devices, such as catheters, that are visible under ultrasound observation.

Ultrasound imaging equipment is increasingly being used during surgical procedures to monitor the location of a device within the body. The visibility of a device under ultrasound depends on various factors including the difference between the acoustic impedance of the material of the device and that of the surrounding medium, such as the patient tissue or body fluid within which the device is located. This difference is relatively low with plastic devices such as catheters and may make conventional catheters difficult to locate. Even devices of metal, such as needles, present problems of visibility under ultrasound observation because of the directional nature of the reflections. In some orientations a metal needle may be clearly visible but in other orientations it may be considerably less visible.

Attempts have been made to increase the visibility of medico-surgical devices under ultrasound observation in various ways. The surface of the device may be modified, such as by forming grooves or indentations in its surface. A reflective coating may be applied to the device, such as incorporating bubbles, as described in WO98/19713 and EP0624342. Alternatively, a metal marker may be secured to a plastics catheter.

BRIEF SUMMARY OF THE INVENTION

It is an object of the present invention to provide an alternative medico-surgical device.

According to one aspect of the present invention there is provided a medico-surgical device of a plastics material, the material including gas bubbles through the major part of the thickness of the material in at least a part of the device such as to increase the visibility of the device under ultrasound imaging.

The device is preferably tubular and the gas bubbles may be provided around the entire circumference of the device or may be provided in a region of the device occupying only a part of the circumference of the device, such as a strip extending along the length of the device. The outer surface of the device may be smooth and uninterrupted by gas bubbles, and the device may have an inner surface that is smooth and uninterrupted by gas bubbles. The bubbles may have a diameter in the range 1µ to 50µ and preferably have a diameter in the range 5µ to 10µ. The bubbles may be substantially spherical. The device may be extruded, the gas bubbles being formed by addition of gas during extrusion of the device. Alternatively, the gas bubbles may be formed by a chemical foaming agent or by the incorporation of hollow microspheres into the plastics material. The plastics material is preferably substantially transparent, the size and density of the bubbles being selected such as to enable material flowing along the device to be viewed by the eye. The plastics material may be polyurethane.

According to another aspect of the present invention there is provided an embryo replacement catheter comprising a flexible, hollow, extruded shaft of a substantially transparent plastics material, the shaft including gas bubbles through the thickness of its wall, the density and size of the bubbles being selected to increase visibility of the catheter under ultrasound imaging whilst enabling an embryo within the catheter to be viewed by the eye, and the bore of the catheter being smooth and uninterrupted by the gas bubbles.

According to a further aspect of the present invention there is provided a method of making a medico-surgical device comprising the steps of extruding a plastics material while incorporating a gas into the wall of the device such as to form gas bubbles through the major part of the thickness of the wall of the device sufficient to increase the visibility of the device under ultrasound observation.

According to a fourth aspect of the present invention there is provided a method of making a medico-surgical device comprising forming a wall of a plastics material containing a chemical foaming agent such as to form gas bubbles through the major part of the thickness of the wall of the device sufficient to increase the visibility of the device under ultrasound observation.

According to a fifth aspect of the present invention there is provided a method of making a medico-surgical device comprising forming a wall of a plastics material containing hollow microspheres such as to form gas bubbles through the major part of the thickness of the wall of the device sufficient to increase the visibility of the device under ultrasound observation.

According to a sixth aspect of the present invention there is provided a device made by a method according to the above further aspect of the present invention.

An embryo-transfer catheter and its method of manufacture, according to the present invention, will now be described, by way of example, with reference to the accompanying drawings.

BRIEF DESCRIPTION OF THE DRAWING

FIG. 1 is a side elevation view of the catheter;

FIG. 2 is a sectional side elevation view of a part of the catheter of FIG. 1 to a larger scale;

FIG. 3 illustrates schematically manufacture of the catheter; and

FIG. 4 is a sectional transverse view through an alternative catheter.

DETAILED DESCRIPTION OF THE PREFERRED EMBODIMENTS

With reference first to FIGS. 1 and 2, the catheter comprises a flexible shaft 1 and a hub 2 joined at the rear end of the shaft. The shaft 1 has a circular section and a bore 10 extending along its length. The shaft 1 opens at its forward, right-hand, patient end 11, which is atraumatically rounded. The shaft 1 is extruded from a clear, transparent polyurethane material and incorporates small, gas-filled bubbles 12 the size and distribution of which are selected to increase the visibility of the catheter under ultrasound observation. Typically, the gas bubbles have a diameter in the range of about 0.1 to 300, preferably being between 1µ and 50µ with the most preferred range being 5µ to 10µ. The bubbles 12 extend through the entire thickness of the wall of the shaft 1 and may be spherical or of any other regular or irregular shape. The outer and inner surfaces 13 and 14 of the shaft may be smooth and uninterrupted by gas bubbles or the bubbles may break the surface.

The hub 2 serves to make connection with the shaft 1 and is moulded from a rigid, transparent plastics material, being subsequently bonded with the rear end of the shaft.

The shaft 1 is extruded in the manner shown in FIG. 3 using an extrusion machine 20. Polyurethane material 21 is heated and supplied to the extrusion head 22 in the usual way but a gas such as nitrogen of carbon dioxide is also injected through the inlet 23 under pressure into the melt. As the plastics emerges from the extrusion head 22 the gas expands to form the bubbles 12. The relatively gas-permeable nature of the plastics means that after manufacture the bubble-forming gas will quickly escape and be replaced with air.

The shaft 1 can be extruded continuously at low cost, without the need for any subsequent operations apart from attaching the hub 2 and end forming the patient end tip 11.

The catheter shaft could be formed by other melt processes, such as injection moulding or blow moulding.

The bubbles could be formed in ways other than by injection of gas into the melt. For example, chemical foaming agents could be added to the plastics material, such as: azocarbonomides, dinitrosopentmethelyene-tetramine, benzenephonohydrazine, 4,4 oxybis(benzenephonohydrazine), $NN^1$dimethyl-$NN^1$ dinitrosoterephthalamide, azoisobutyronitrile, sodium bicarbonate, terephthalazide or trihydrazinatrazine. Another way of forming the gas bubbles would be by incorporating a liquid into the plastics melt which volatises during the melt process. Alternatively, solid powdered dry ice (carbon dioxide) could be incorporated into the melt so that the particles of dry ice become gas bubbles during the forming process. It might be possible to use other solids which undergo sublimation in this way. The bubbles could be formed directly as a result of chemical reaction during polymerisation and or alternatively during cross-linking. The bubbles could be formed mechanically by whipping the plastics in a liquid form, such as in the manner used to form latex foam. The bubbles could be formed by the incorporation of hollow microspheres of resin or glass. Alternatively, small particles of a soluble material could be added to the plastics melt and subsequently dissolved away.

A shaft of this kind can have good visibility under ultrasound imaging without producing multiple echoes and can produce a good image regardless of the orientation of the shaft. The shaft can be made sufficiently transparent to ultrasound energy to enable material flowing along the bore of the catheter to be observed on the ultrasound image.

Because the catheter does not require any coating or separate marker there is no need for subsequent assembly operations and there is no risk of detachment. The catheter can be made of conventional medically-approved materials so does not present any new risk to the patient. Because the surface of the catheter can be smooth, the catheter can be inserted or slid through an outer tube with low friction. The smooth bore of the catheter ensures free flow along the bore, which can be important where the catheter is used to transfer embryos. The smooth surfaces also reduce the accumulation of biofilm on the catheter. The catheter can be made without the need for metal components, which can be an advantage where the catheter is used while the patient is being viewed by magnetic imaging techniques. The catheter can be completely transparent to x-rays or the plastics from which it is formed could incorporate an x-ray opaque filler, such as barium sulphate.

The bubble size and density can be selected so that the optical transparency of the plastics forming the shaft remains sufficient to enable material flowing along the shaft to be viewed by the eye.

There are various ways in which the catheter could be modified. For example, it could be preferable for the bubbles to have a non-spherical shape and be oriented in a particular direction, such as longitudinally. This could be achieved by means of an obstruction in the extrusion die that constricts and elongates the bubbles as they flow through. Such an arrangement may give an increase in ultrasound visibility whilst reducing the opacity of the shaft to the eye.

It is not essential for the bubbles to be provided around the entire circumference of the shaft. As shown in FIG. 4, the bubbles 12' could be formed only in one or more stripes extending along the shaft 1', such as in the stripe 40. This arrangement can be used where the shaft needs to have increased clarity so that material within the catheter can be seen by the eye. The bubble region need not be continuous along the length of the catheter. Instead, discrete separate regions with bubbles could be separated from one another along the length of the catheter by regions without bubbles. A shaft for such a catheter could be made by interrupting gas flow to the extruder. Where the bubbles are contained within a stripe, this could be interrupted to make it discontinuous by extruding the stripe using two auxiliary extruders, one having material with a blowing agent and the other having material without the blowing agent. Alternate extruders are switched on and off so that the stripe can have sections containing bubbles separated from one another by sections without bubbles. A catheter with an interrupted bubble region may give a clearer ultrasound indication of movement of the catheter along its length and may also enable clearer observation of material flowing along the catheter both by ultrasound and by the eye.

What I claim is:

1. An embryo replacement catheter comprising:
   a hub; and
   a shaft attached to the hub, the shaft having a bore extending therethrough, the shaft comprising a wall of a transparent plastic material with gas bubbles incorporated therein,
   wherein the gas bubbles extend through a major part of a thickness of the wall of the shaft, and the gas bubbles have a density and size to enable visibility of the catheter under ultrasound imaging and to enable an embryo within the bore of the shaft to be viewed by a naked eye of a user.

2. The embryo replacement catheter of claim 1, wherein an outer surface of the wall of the shaft forms an outer surface of the catheter.

3. The embryo replacement catheter of claim 2, wherein the shaft has an inner surface that is smooth and uninterrupted by the gas bubbles.

4. The embryo replacement catheter of claim 1, wherein the bore is smooth and uninterrupted by the gas bubbles.

5. The embryo replacement catheter of claim 1, wherein the shaft is tubular.

6. The embryo replacement catheter of claim 1, wherein the shaft is flexible.

7. The embryo replacement catheter of claim 1, wherein the gas bubbles extend around an entire circumference of the shaft.

8. The embryo replacement catheter of claim 1, wherein the gas bubbles extend around a first portion of a circumference of the shaft, a second portion of the circumference of the shaft being free of the gas bubbles.

9. The embryo replacement catheter of claim 1, wherein the shaft has an outer surface that is smooth and uninterrupted by the gas bubbles.

10. The embryo replacement catheter of claim 1, wherein the shaft has an inner surface that is smooth and uninterrupted by the gas bubbles.

11. The embryo replacement catheter of claim 1, wherein the gas bubbles have a nominal diameter of 1μ to 50μ.

12. The embryo replacement catheter of claim 1, wherein the gas bubbles have a nominal diameter of 5μ to 10μ.

13. The embryo replacement catheter of claim 1, wherein the gas bubbles are substantially spherical.

14. The embryo replacement catheter of claim 1, wherein the shaft is extruded, and the gas bubbles are formed by introducing gas to the plastic material, in a molten state, during extrusion of the shaft.

15. The embryo replacement catheter of claim 1, wherein the plastic material is polyurethane.

16. The embryo replacement catheter of claim 1, wherein the hub is formed of a transparent material.

17. The embryo replacement catheter of claim 16, wherein the transparent material is a plastic.

\* \* \* \* \*